United States Patent [19]
Kim

[11] Patent Number: 5,972,200
[45] Date of Patent: *Oct. 26, 1999

[54] METHOD FOR DRIVING A WIDE RANGE AIR TO FUEL RATIO SENSOR

[75] Inventor: Byung-ki Kim, Kyungki-do, Rep. of Korea

[73] Assignee: Samsung Electro-Mechanics Co., Ltd., Kyungki-do, Rep. of Korea

[ * ] Notice: This patent issued on a continued prosecution application filed under 37 CFR 1.53(d), and is subject to the twenty year patent term provisions of 35 U.S.C. 154(a)(2).

[21] Appl. No.: 08/578,131

[22] Filed: Dec. 26, 1995

[30] Foreign Application Priority Data

Dec. 26, 1994 [KR] Rep. of Korea ........................ 94-36927
May 31, 1995 [KR] Rep. of Korea ........................ 95-14410

[51] Int. Cl.$^6$ .................................................. G01N 27/407
[52] U.S. Cl. ........................ 205/784.5; 204/424; 204/425; 204/426; 204/427
[58] Field of Search ................................. 204/421–429; 205/783.5, 784, 784.5, 785

[56] References Cited

U.S. PATENT DOCUMENTS

| | | | |
|---|---|---|---|
| 4,264,425 | 4/1981 | Kimura et al. .......................... | 204/425 |
| 4,496,455 | 1/1985 | Linder et al. .......................... | 204/425 |
| 4,574,627 | 3/1986 | Sakurai et al. .......................... | 204/426 |
| 4,769,124 | 9/1988 | Okada et al. .......................... | 204/425 |
| 4,776,943 | 10/1988 | Kitahara .................................. | 204/427 |
| 4,882,033 | 11/1989 | Shibata et al. .......................... | 204/425 |
| 5,360,528 | 11/1994 | Oh et al. .................................. | 204/425 |

OTHER PUBLICATIONS

Solid State Ionics 86–88 (1996) month available 1079–1085, B. Kim, J. Lee and H. Kim; Samsung Advanced Institute of Technology.

Tessho Yamada, Universal Air–Fuel Ratio Heated Exhause Gas Oxygen Sensor And Further Applications, No. 920234, pp. 23–36. date unavailable.

*Primary Examiner*—T. Tung
*Attorney, Agent, or Firm*—Foley & Lardner

[57] ABSTRACT

A wide range air to fuel (A/F) ratio sensor having a solid electrolyte plate, a measurement electrode and a first pumping electrode both formed at one surface of the solid electrolyte plate, the measurement electrode serving as both an oxygen pumping electrode and a sensing electrode, and a second pumping electrode and a sensing reference electrode both formed at another surface of the solid electrolyte plate, the sensing reference electrode being supplied with oxygen from the first pumping electrode and thereby serving as an oxygen reference electrode. The wide range A/F ratio sensor can be driven by a reference voltage variation method which adds a surplus voltage to a reference voltage.

11 Claims, 4 Drawing Sheets

METHOD FOR DRIVING A WIDE RANGE AIR TO FUEL RATIO SENSOR

BACKGROUND OF THE INVENTION

1. Field of the Invention

The present invention relates to an oxygen sensor and a method for driving the same and, more particularly, to a wide range air to fuel (A/F) ratio sensor utilizing the characteristics of oxygen concentration and oxygen pumping cells made of a solid electrolyte such as YSZ ($Y_2O_3$ stabilized $ZrO_2$) and a method for driving such a wide range A/F ratio sensor.

2. Description of the Prior Art

Oxygen sensors utilizing the characteristic of oxygen concentration cells made of a solid electrolyte such as YSZ are being widely used for the purpose of, for example, controlling the A/F ratio in automobiles. Recently, developments have been made in wide range A/F ratio sensors which utilize the oxygen ion migration characteristic of a solid electrolyte and the oxygen concentration cell characteristic. Such wide range A/F ratio sensors have an advantage that they can be used to control the air to fuel ratio over a wide range from fuel rich to fuel lean.

However, conventional wide range A/F ratio sensors have a significant problem in that their manufacture is difficult due to their complex structure. Furthermore, it is difficult to ensure the reproducibility. FIG. 1 illustrates schematically a typical wide range A/F ratio sensor being used in an actual situation. As shown in FIG. 1, the A/F ratio sensor includes an oxygen pumping cell 1 and a sensing cell 3 both laminated independently of each other. Between the cells 1 and 3, a porous diffusion passage is provided which defines a diffusion chamber 2. Due to such complex structure, the A/F ratio sensor is difficult to manufacture (Society of Automobile Engineers 920234).

In particular, this A/F ratio sensor requires a time interval for sending a variation in the concentration of gas, occurring upon pumping oxygen, to the sensing electrode. Such a time interval results in a delayed response of sensing and an increase in the operation pumping voltage over a required level. In addition, the A/F ratio sensor has a structural limitation. In other words, the space between the sensing electrode and the pumping electrode must be appropriately adjusted.

On the other hand, FIG. 2 illustrates another A/F ratio sensor suggested in U.S. Pat. No. 4,776,943. This patent describes that the problem involved in the A/F ratio sensor structure of FIG. 2 may be eliminated by adapting the appropriate AC circuit. In the 4,776,943 patent, however, no concrete mechanism or method is taught. Moreover, since this A/F ratio sensor has a pumping electrode 12 exposed to air as shown in FIG. 2, a voltage is generated due to an oxygen partial difference between pumping electrodes 11 and 12 even when no pumping voltage is applied. This A/F ratio sensor also has a fundamental problem of requiring the inevitable application of surplus pumping voltage upon measuring a lean region. Due to such problems, it is difficult to use this A/F ratio sensor as a wide range sensor.

SUMMARY OF THE INVENTION

Therefore, an object of the invention is to provide an A/F ratio sensor capable of measuring the air to fuel ratio over a wide range, with high flexibility in the design of the diffusion barrier, and superior reproducibility and reliance for long-term use.

Another object of the invention is to provide a method for driving an A/F ratio sensor, capable of measuring the air to fuel ratio over a wide range, to obtain superior reproducibility and ensure reliance for long-term use.

In one aspect, the present invention provides a wide range A/F ratio sensor with a sensor unit and a heater unit, wherein the sensor unit has a solid electrolyte plate; a measurement electrode and a first pumping electrode both formed at one surface of the solid electrolyte plate, the measurement electrode serving as both an oxygen pumping electrode and a sensing electrode; and a second pumping electrode and a reference electrode both formed at the other surface of the solid electrolyte plate, the reference electrode being supplied with oxygen from the first pumping electrode and thereby serving as an oxygen reference electrode.

In another aspect, the present invention provides a method for driving a wide range A/F ratio sensor including a sensor unit and a heater unit, the sensor unit including a solid electrolyte plate, a measurement electrode and a first pumping electrode both formed at one surface of the solid electrolyte plate, the measurement electrode serving as both an oxygen pumping electrode and a sensing electrode, and a second pumping electrode and a reference electrode both formed at the other surface of the solid electrolyte plate, the reference electrode being supplied with oxygen from the first pumping electrode and thereby serving as an oxygen reference electrode. The method includes measuring the value of a resistance between the measuring electrode and the second pumping electrode; determining a surplus voltage generated between the measurement electrode and the reference electrode, which depends on the value of a pumping current existing between the measurement electrode and the second pumping electrode, on the basis of the measured resistance value; and adding the surplus voltage to a reference voltage.

In yet another aspect, the present invention provides a method for driving a wide range A/F ratio sensor including a sensor unit and a heater unit, the sensor unit including a solid electrolyte plate, a measurement electrode and a first pumping electrode both formed at one surface of the solid electrolyte plate, the measurement electrode serving as both an oxygen pumping electrode and a sensing electrode, and a second pumping electrode and a reference electrode both formed at the other surface of the solid electrolyte plate, the reference electrode being supplied with oxygen from the first pumping electrode and thereby serving as an oxygen reference electrode. The method includes measuring a pumping voltage of the oxygen sensor; and adding a value proportional to the pumping voltage to a reference voltage.

BRIEF DESCRIPTION OF THE DRAWINGS

Other objects and aspects of the invention will become apparent from the following description of embodiments with reference to the accompanying drawings in which.

DESCRIPTION OF THE PREFERRED EMBODIMENTS

Solid electrolytes such as YSZ, MSZ and CSZ respectively containing $ZrO_2$ stabilized by solid solutions of $Y_2O_3$, MgO and CaO in small amounts generate an electromotive force EMF expressed by the following Nernst's equation when a difference in oxygen concentration exists across the solid electrolyte:

$$EMF = (RT/4F) \cdot ln(P_{o1}/P_{o2}) \tag{1}$$

where, R is the gas constant, T is the absolute temperature, F is the Faraday constant, and $P_{o1}$ and $P_{o2}$ are the oxygen partial pressures.

On the contrary, a flow of current is generated when a voltage is applied across the electrolyte. In this case, oxygen ions serve as carriers. Accordingly, it is possible to migrate oxygen through the solid electrolyte. Such a property is called "oxygen pumping". By combining the above-mentioned two characteristics, it is possible to measure the A/F ratio over a wide range.

Figure 3:
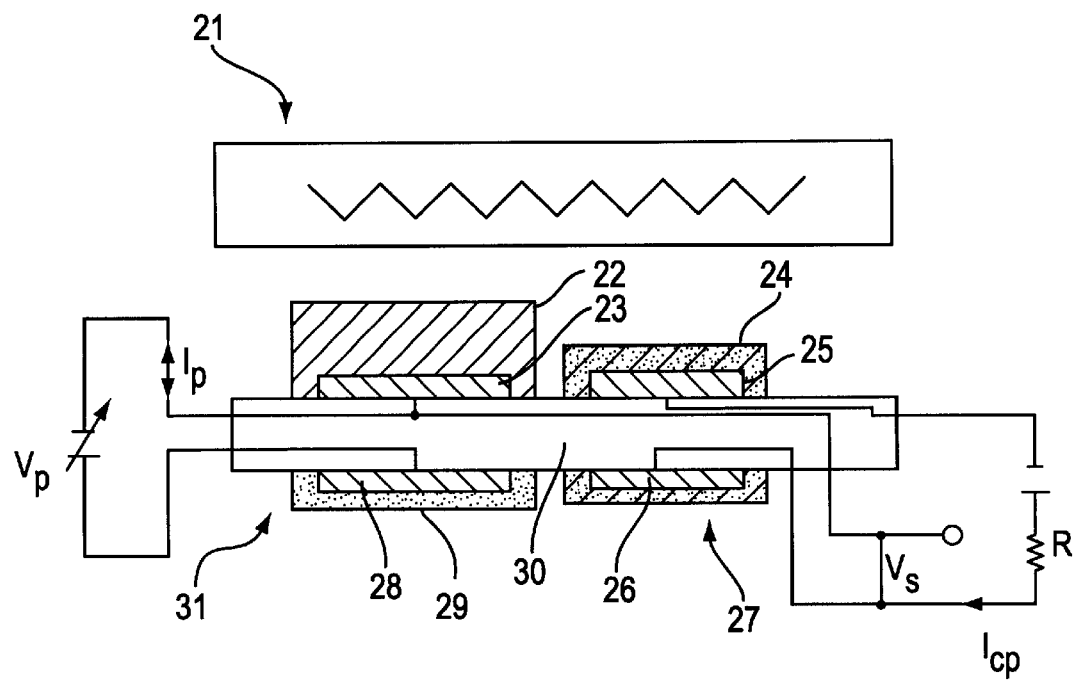
FIG. 3 is a schematic view illustrating a wide range A/F ratio sensor in accordance with the present invention.

Referring to FIG. 3, there is illustrated a wide range A/F ratio sensor in accordance with the present invention. This wide range A/F ratio sensor has a structure for sharing a measurement electrode using an oxygen pumping cell and a sensing cell both formed on a single solid electrolyte plate so that the measurement electrode can serve as both an oxygen pumping electrode and a sensing electrode. This structure will be described in detail in conjunction with FIG. 3.

The wide range A/F ratio sensor of the present invention comprises a sensor unit and a heater unit which are denoted by the reference numerals 31 and 21, respectively. The heater unit 21 serves to maintain the sensor unit 31 at a temperature ranging from 500° C. to 900° C.

The sensor unit 31 includes a plate 30 made of a solid electrolyte basically containing $ZrO_2$ exhibiting oxygen ion conducting characteristics. The solid electrolyte plate 30 is provided at its upper surface with a porous Pt electrode 23 serving as a common electrode adopted to pump oxygen and simultaneously measure the concentration of the oxygen of the electrode. On one side of the common electrode 23, another porous Pt electrode as an oxygen pumping electrode 25 is provided at the upper surface of the solid electrolyte plate 30. The oxygen pumping electrode 25 pumps oxygen to electrode 26 as microcurrent flows therethrough. Two porous Pt electrodes are also provided at the lower surface of the solid electrolyte plate 30. One of the lower electrodes serves as an oxygen reference electrode 26 whereas the other lower electrode serves as a pumping electrode 28. The electrode 26 is coated with a porous insulating material. The electrode 26 receives oxygen pumped from the oxygen pumping electrode 25 so that it can be used as an oxygen reference chamber.

The microcurrent used to provide the oxygen reference chamber which is denoted by the reference numeral 27 in FIG. 3 can be obtained by connecting a voltage source supplying a certain voltage of, for example, 2 to 6 V and a resistor of several kilo-ohms or several tens of kilo-ohms in series between the electrodes 25 and 26.

When the current required to provide the oxygen reference chamber 27 has a very small intensity, for example, about 10 µA, one of the electrodes 23 and 28 may be selected as the electrode providing the oxygen to the reference electrode in place of the electrode 25. Such an optional oxygen reference chamber 27 may be replaced by an air reference electrode. In this case, the air reference electrode should be selectively formed on the sensing reference electrode 26.

Meanwhile, a diffusion barrier layer 22 is formed over the electrode 23. The diffusion barrier layer 22 serves to inhibit diffusion of gases so that a limiting current is exhibited. The diffusion barrier layer 22 may have a porous structure or a pin hole structure. Other structures used in the existing limiting current type oxygen sensors may also be used as the diffusion barrier.

Porous protection layers 24 and 29 are formed over the pumping electrodes 25 and 28 to prevent the electrodes from being directly exposed to an exhaust gas to be measured, respectively.

Basically, the existing wide range A/F ratio sensors are driven by a pumping voltage applied such that a sensing voltage reaches a reference voltage ranging from 450 mV to 500 mV, to measure the value of the current generated by applying the pumping voltage. In accordance with the present invention, however, a variable reference voltage is also selected.

Now, the principle of the wide range A/F ratio sensor according to the present invention will be described in detail. The driving principle of this A/F ratio sensor will be described in conjunction with the detection of the air to fuel ratio in an automobile.

As exhaust gases are generated from the automobile, an oxygen partial pressure $P_{o1}$ is measured around the measurement electrode of the oxygen sensor. As a result, the sensing cell generates an electromotive force. If the air to fuel ratio of the exhaust gas is higher than the stoichiometric air to fuel ratio, the generated electromotive force is very low, for example, only about 100 mV. When the air to fuel ratio of the exhaust gas is lower than the stoichiometric air to fuel ratio, a high electromotive force of, for example, 900 mV is generated. Thus, the sensing cell can determine whether or not the amount of air supplied is excessive, on the basis of the electromotive force. When the amount of supplied air is excessive, the oxygen existing around the measurement electrode is extracted by the pumping cell so that the oxygen concentration around the measurement electrode is lowered to a desired level at which an electromotive force of about 450 mV is generated. Where the diffusion of oxygen is the rate-determining step, the pumping current $I_p$ flowing through the pumping cell at this time has a relationship with the amount of oxygen diffused through the diffusion barrier, as follows:

$$I_p = (4FDS/RTL) \times (P_{o1} - P_{os}) \tag{2}$$

where, D is the diffusion coefficient of $O_2$, S the cross-sectional area of the gas diffusion path, L the length of the gas diffusion path, $P_{o1}$ the oxygen partial pressure in the exhaust gas, and $P_{os}$ oxygen partial pressure in the measurement electrode (electrode 23).

When the electromotive force $V_s$ generated from the sensing cell is equal to 450 mV, accordingly, the pumping current $I_p$ is proportional to the oxygen partial pressure $P_{o1}$ of the exhaust gas because the partial pressure $P_{os}$ is approximately zero.

On the other hand, when the amount of supplied air is less than its stoichiometry, the pumping current $I_p$ flows reversely, that is, in a direction in which oxygen is supplied to the measurement electrode. In this case, the supplied oxygen reacts with CO, $H_2$ and HC components of the exhaust gas present around the measurement electrode. As the gas components are consumed by the reaction with the oxygen, the electromotive force $V_s$ generated from the sensing cell is decreased. Thus, the electromotive force $V_s$ of 450 mV can be obtained by controlling the flow of the pumping current $I_p$. In this connection, the following equation can be established:

$$-I_p=(2FDS/RTL)\times(P_{c1}-P_{cs}) \quad (2\text{-}1)$$

In equation (2-1), D is the diffusion coefficient of CO or $H_2$, $P_{c1}$ the partial pressure of the exhaust gas such as CO or $H_2$ outside the oxygen sensor, and $P_{cs}$ the partial pressure of the exhaust gas such as CO or $H_2$ in the measurement electrode 23.

Since the pumping current $I_p$ is proportional to the air to fuel ratio when it is controlled to obtain the electromotive force $V_s$ of 450 mV, it is possible to measure the air to fuel ratio or the oxygen concentration by measuring the pumping current $I_p$.

Figure 1:
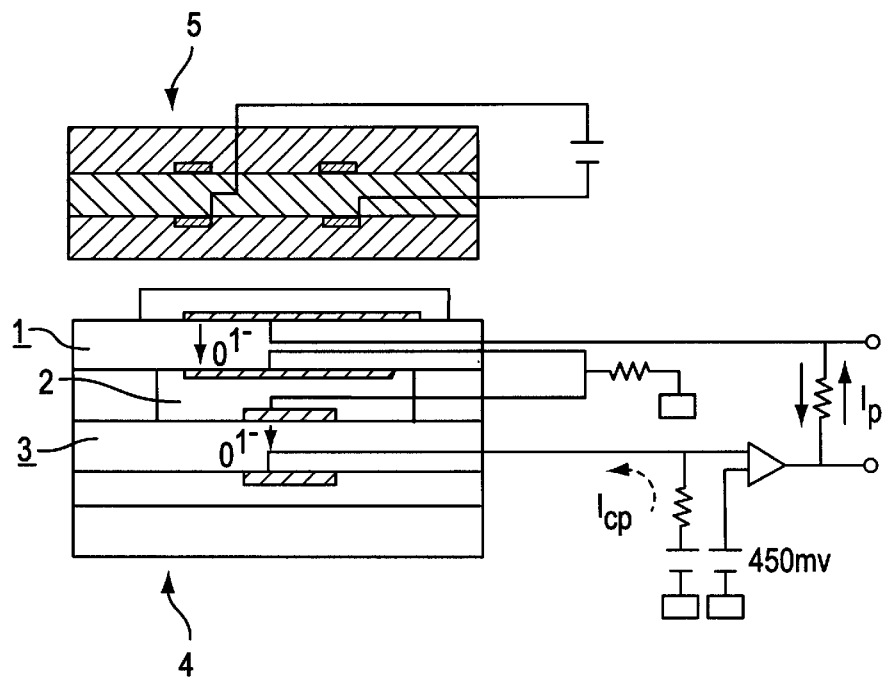
FIG. 1 is a schematic view illustrating a conventional wide range A/F ratio sensor.
Figure 2:
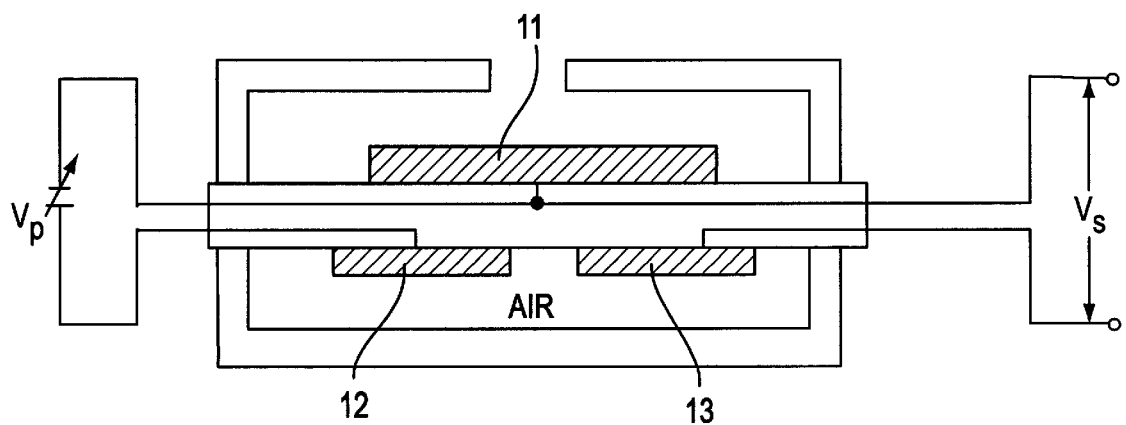
FIG. 2 is a schematic view illustrating another conventional wide range A/F ratio sensor.

The above-mentioned principle is established in the case where the sensing cell and the pumping cell do not share the solid electrolyte with each other, as shown in FIG. 1. In the case where the sensing cell and the pumping cell share the solid electrolyte and the measurement electrode with each other, it is necessary to take into consideration the influence of the shared elements in order to extend the sensing range.

Figure 4:
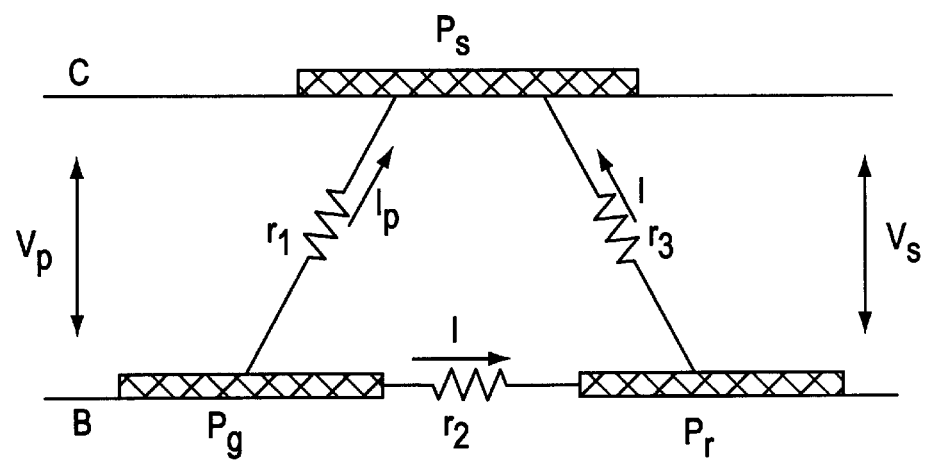
FIG. 4 is a schematic view explaining the operation principle of the wide range A/F ratio sensor shown in FIG. 3.

FIG. 4 is a diagram for explaining the operation concept of the A/F ratio sensor related with its three electrodes except for the electrode 26 for providing the oxygen reference chamber 27. The influence of the electrode 26 is negligible because microcurrent flows through the electrode 26.

When the concentration of oxygen contained in an initial exhaust gas is $P_g$, the pumping voltage $V_p$ applied between two electrode positions a and b can be expressed by the following equation:

$$\begin{aligned}V_p &= I_p \times r_1 + (RT/4F)\cdot \ln(P_g/P_s) \quad (3)\\ &= I\times r_2 + (RT/4F)\cdot \ln(P_g/P_r) + I\times r_3 + (RT/4F)\cdot \ln(P_r/P_s)\end{aligned}$$

where, $P_r$ is an oxygen partial pressure at the oxygen reference electrode, and $P_s$ is an oxygen partial pressure at the measurement electrode.

In equation (3), $r_1$, $r_2$ and $r_3$ are resistances each coupled between electrodes. For solid electrolytes having the same intrinsic property, accordingly, the resistances vary depending on the size of each electrode, the arrangement of electrodes and the thickness of the solid electrolyte used. Since the sensing voltage $V_s$, which is an actually measured value, corresponds to "$I\times r_3+(RT/4F)\cdot\ln(P_r/P_s)$" in the equation (3), the value "$I\times r_3$" may be a surplus voltage resulting from sharing the electrode and electrolyte.

In the wide range A/F ratio sensor according to the present invention, a limiting current proportional to the air to fuel ratio is measured. Where a large quantity of $CO_2$ or $H_2O$ exists in the exhaust, such a limiting current is exhibited when over voltage "$(RT/4F)\cdot\ln(P_r/P_s)$" ranges between 0.2 and 0.8. Accordingly, the sensor should be driven to satisfy the above condition. Meanwhile, "$I_p\times r_1$" is increased when the pumping voltage $V_p$ initiating the generation of the limiting current is increased. Such an increase in "$I_p\times r_1$" results in an increase in the surplus voltage "$I\times r_3$" being added to the sensing voltage $V_s$. As a result, a driving pumping voltage corresponding to the sensing voltage reaching the reference voltage of, for example, 450 mV is shifted to the initial region starting the limiting current. Furthermore, there is a problem that the sensing voltage reaches 450 mV, namely, the reference voltage, before a desired limiting current is generated.

In accordance with the present invention, the surplus voltage, namely, "$I\times r_3$" is added to the reference voltage in order to extract only the value "$(RT/4F)\cdot\ln(P_r/P_s)$" obtained by removing the value "$I\times r_3$" from the sensing voltage.

By re-arranging the equation (3), the following equation can be derived:

$$I_p\times r_1=I\times r_2+I\times r_3$$

This equation can be re-arranged as follows:

$$I\times r_3=I_p\times r_1\times r_3/(r_2+r_3) \quad (4)$$

where, "$r_3/(r_2+r_3)$" is a constant related to the structure of the wide range A/F ratio sensor.

The constant "$r_3/(r_2+r_3)$" can be experimentally measured and set, and ranges from ¼ to ½. After the resistance of the resistor $r_1$ between the pumping electrodes 23 and 28 is measured, the value "$I\times r_3$" depending on "$I_p$" can be determined by using Eq. (4). For example, the reference voltage, $V_r$, may be varied by coupling a series resistor $kr_1$ (k=¼ to ½, and $r_1$ is a constant) to the pumping cell resistance $r_1$ and then adding a voltage drop generated across the series resistor to the reference voltage $V_r$. In other words, the reference voltage becomes a variable reference voltage $V_r'$ having a value of "450 mV+$I_p\times kr_1$". When the resistance of the pumping cell is varied after a prolonged use of the A/F ratio sensor, this variation is compensated by appropriately adjusting the variable reference voltage $V_r'$. For such a variation, the resistor $kr_1$ is constituted by a variable resistor. In other words, the resistor provided for obtaining the resistance $kr_1$ is a variable resistor having a resistance variable depending on "$r_1$".

Alternatively, a part of the pumping voltage may be added to the reference voltage. This method can be easily achieved even though it provides an accuracy slightly less than that of the above-mentioned method. It is possible to greatly extend the measurement range by varying the reference voltage $V_r$ in proportion to the pumping voltage $V_p$ as follows:

$$V_r'=450\ mV+K\times V_p (k=\text{⅕ to ½})$$

where $V_r'$ is the variable reference voltage.

In this case, the constant K is determined mainly depending on the structure of the wide range A/F ratio sensor and is easily determined through an experiment.

The present invention will be understood more readily with reference to the following examples; however, these examples are intended to illustrate the invention and are not to be construed to limit the scope of the present invention.

EXAMPLE 1

In order to fabricate a wide range A/F ratio sensor, a green sheet having a thickness of 0.6 mm was prepared as a solid electrolyte 30 using a doctor blade method. The green sheet was made of 8YSZ which is widely used for automobile oxygen sensors. Pt electrodes were then printed on opposite surfaces of the green sheet to make electrodes 23, 25, 26 and 28 respectively for a sensor cell and a pump cell, as shown in FIG. 3.

Meanwhile, alumina for grinding was mixed with 8YSZ in a weight ratio of 1:1 to produce a mixture paste thereof.

The used alumina had a particle size of about 1 μm whereas the used 8YSZ had a particle size of about 0.05 μm. The paste was then coated over the electrode 23 using a screen printing method, thereby forming a diffusion barrier layer 22 over the electrode 23. Another paste was also prepared by mixing alumina for grinding (having a particle size of about 1 μm) with YSZ (having a particle size of about 0.05 μm) in a weight ratio of 1:5. The latter paste was then coated over the electrode 26 using the screen printing process, thereby forming an oxygen reference chamber 27.

On the other hand, the remaining electrodes 25 and 28 were coated with a paste produced by mixing alumina (having a particle size of about 3 μm) with 10 wt. % 8YSZ (having a particle size of about 0.05 μm) for protection layers. In this coating step, the same screen printing method as above was used. A heater 21 was also made by printing a Pt electrode on an alumina sheet having a thickness of 0.8 mm.

Figure 5:
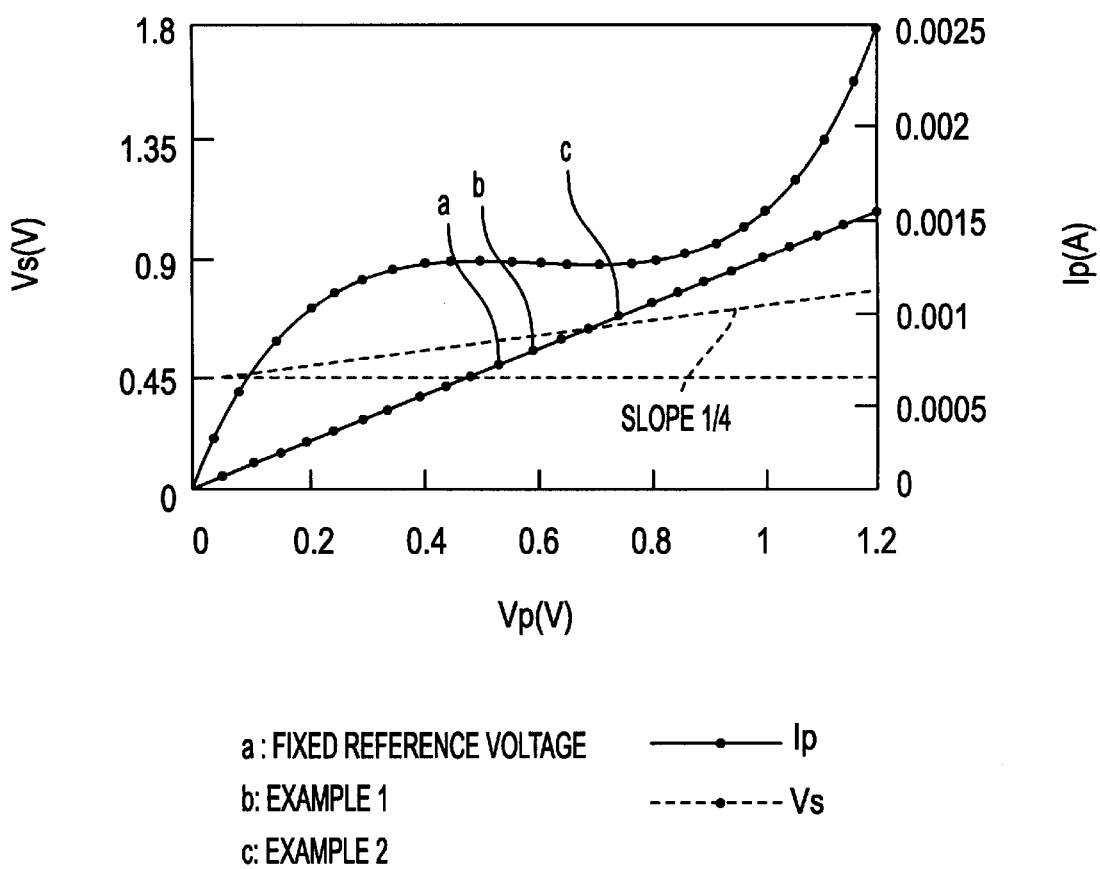
FIG. 5 depicts graphs respectively showing variations in pumping current $I_p$ and sensing voltage $V_s$ depending on the pumping voltage $V_p$ in the wide range A/F ratio sensor of FIG. 3 in the presence of 3% $O_2$ and 10% $CO_2$.
Figure 6:
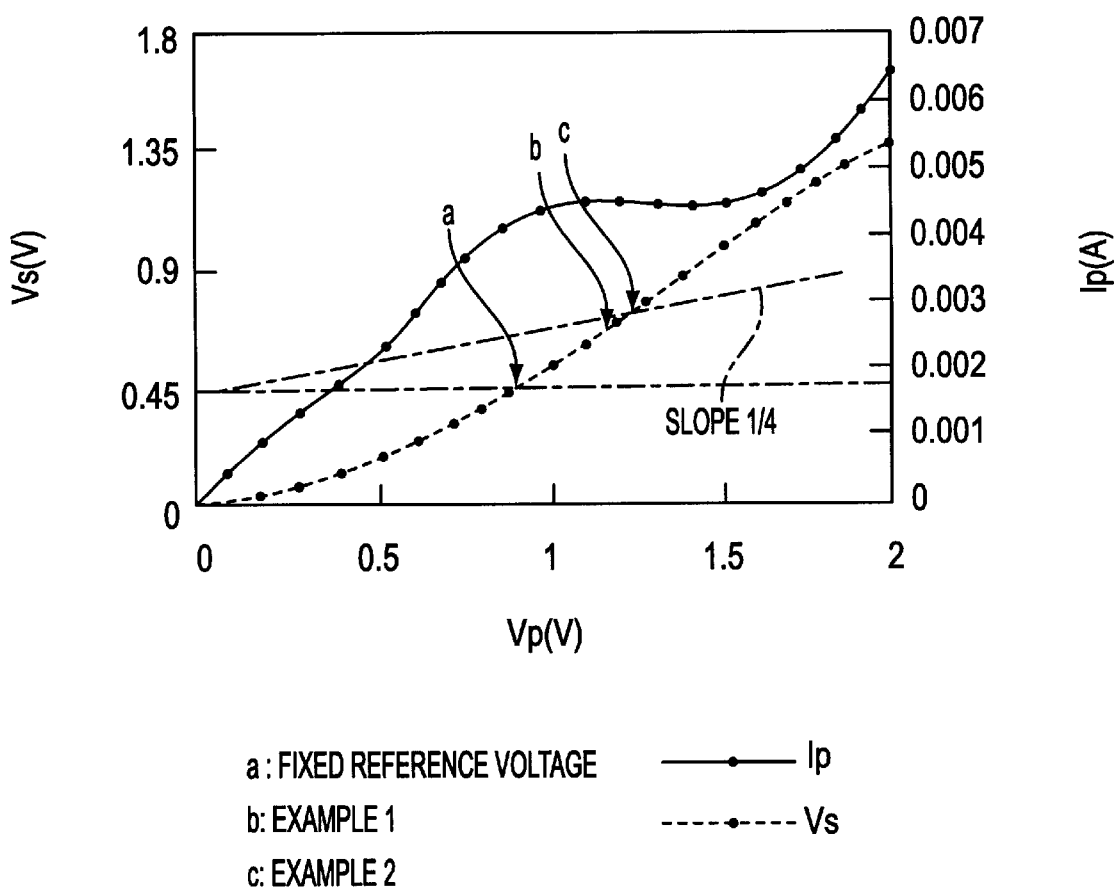
FIG. 6 depicts graphs respectively showing variations in pumping current $I_p$ and electromotive force $V_s$ depending on the pumping voltage $V_p$ in the wide range A/F ratio sensor of FIG. 3 in the presence of 10% $O_2$ and 10% $CO_2$.

An artificial exhaust gas test was carried out for $N_2$, $O_2$ and $CO_2$ gases. The results are depicted in FIGS. 5 and 6.

For the wide range A/F ratio sensor fabricated in the above-mentioned manner, resistances individually existing between electrodes coupled to each other were measured using a multi-meter. After substituting the measured resistances for the equation (4) ($I \times r_3 = I_p \times r_1 \times r_3 / (r_2+r_3)$), the value "$r_3/(r_2+r_3)$" was $\frac{1}{3}$. That is, the value "$I \times r_3$" was "$I_p \times r_1 \times \frac{1}{3}$". By adding the value "$I \times r_3$" to the reference voltage $V_r$, namely, 450 mV, a variable reference voltage $V_r'$ corresponding to "450 mV+$I_p \times r_1 \times \frac{1}{3}$" was obtained. In this case, the resistance $r_1$ was 150 Ω.

EXAMPLE 2

A part of the pumping voltage was added to the reference voltage $V_r$ of 450 mV to obtain a variable reference voltage $V_r'$ corresponding to "450 mV+$K \times V_p$ (K=¼). In this case, the constant K was determined by deriving a value for "K" satisfying "$V_p$" ranging from 0.5 V to 2.5 V in the equation of "$I \times r_1 = I_p \times r_1 \times \frac{1}{3} = \frac{1}{3}(V_p - 0.45) \approx KV_p$". The derived K's value was about ¼.

FIG. 5 depicts graphs respectively showing variations in $I_p$ and $V_s$ depending on the pumping voltage $V_p$ in the wide range A/F ratio sensor in the presence of 3% $O_2$ and 10% $CO_2$ in accordance with the examples. On the other hand, FIG. 6 depicts graphs respectively showing variations in $I_p$ and $V_s$ depending on the pumping voltage $V_p$ in the wide range A/F ratio sensor in the presence of 10% $O_2$ and 10% $CO_2$ in accordance with the examples.

For the A/F ratio sensor not using a variable reference voltage, "$I_p$" exists within the limiting current region (shown by a horizontal graph zone) when the concentration of $O_2$ is 3% under a condition that the reference voltage is set by 450 mV, as shown by the graph "a" of FIG. 5. When the concentration of $O_2$ is increased to 10%, "$I_p$" corresponding to "$V_s$" of 450 mV is less than the limiting current, as shown by the graph "a" of FIG. 6. As a result, the A/F ratio sensor not using a variable reference voltage can not possibly measure the oxygen concentration above 10%. In both cases by adding the value "$I \times r_3$" to "$V_s$" or by adding a part of the pumping voltage to the reference voltage, the "$I_p$" is present within the limiting current region even when the concentration of $O_2$ is above 10%, as shown by graphs "b" and "c" in FIG. 6.

The graphs "b" in FIGS. 5 and 6 corresponding to Example 1 show a variation in the value "$I_p$" under a condition that the reference voltage is varied in the above-mentioned fashion. Referring to these graphs "b", it can be found that the value "$I_p$" is present in the limiting current region every time.

The graphs "c" in FIGS. 5 and 6 corresponding to Example 2 show a variation in the value "$I_p$" under a condition that the reference voltage is varied in the above-mentioned fashion. Referring to these graphs "c", it can be found that the value "$I_p$" exists in the limiting current region every time. Example 2 has an advantage that the measurement can be achieved more easily even though its range is more or less limited, as compared to Example 1.

In particular, the wide range A/F ratio sensor using the variable reference voltage in accordance with the present invention is effective as explained below.

First, it is possible to measure the air to fuel ratio over a wide range.

Second, a high flexibility is provided in the design of the diffusion barrier. For avoiding problems caused by the solid electrolyte and electrode sharing, a low pumping voltage is required. The design of the diffusion layer should be made, taking into consideration the requirement associated with the pumping voltage. Since the problem caused by electrode sharing is solved in accordance with the present invention, the design of the diffusion barrier is more flexible.

Third, a superior reproducibility is obtained. Since a high flexibility is provided in the design of the diffusion barrier in accordance with the present invention, it is required to compensate only a deviation caused by a variation of the diffusion barrier.

Fourth, reliability is ensured for long-term use. An increased improvement in long-term stability is obtained because the sensor characteristics obtained in accordance with the present invention is independent of a variation in the resistance generated during the use of the sensor.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A method of driving a wide range air to fuel (A/F) ratio sensor having a sensor unit and a heater unit, the sensor unit comprising a solid electrolyte plate, a measurement electrode being formed at one surface of the solid electrolyte plate, the measurement electrode serving as both an oxygen pumping electrode and a sensing electrode, and a second pumping electrode and a sensing reference electrode both formed at another surface of the solid electrolyte plate, the sensing reference electrode being supplied with oxygen and thereby serving as an oxygen reference electrode, comprising the steps of:

measuring the value of a resistance between the measuring electrode and the second pumping electrode;

applying a pumping voltage between the measurement electrode and the second pumping electrode to generate a pumping current;

determining a surplus voltage generated between the measurement electrode and the sensing reference electrode depending on the value of the pumping current, on the basis of the value of a resistance between the measuring electrode and the second pumping electrode; and adding the surplus voltage to a reference voltage to generate a variable reference voltage value;

controlling the pumping current to maintain a sensing voltage between the measurement electrode and the sensing reference electrode substantially at the variable reference voltage value; and determining the value of the pumping current to determine an air to fuel ratio or oxygen concentration of a gas supplied to the sensor.

2. A method as claimed in claim 1, wherein the resistance for adding the surplus voltage to a reference voltage is a variable resistance.

3. A method as claimed in claim 1, wherein the surplus voltage generated between the measurement electrode and the sensing reference electrode corresponds to ¼ to ½ of a product of the resistance between the measurement electrode and the second pumping electrode by the pumping current value between the measurement electrode and the second pumping electrode.

4. A method of driving a wide range air to fuel (A/F) ratio sensor having a sensor unit and a heater unit, the sensor unit comprising a solid electrolyte plate, a measurement electrode formed at one surface of the solid electrolyte plate, the measurement electrode serving as both an oxygen pumping electrode and a sensing electrode, and a second pumping electrode and a reference electrode both formed at the other surface of the solid electrolyte plate, the reference electrode being supplied with oxygen and thereby serving as an oxygen reference electrode, comprising the steps of:

applying a pumping voltage between the measurement electrode and the second pumping electrode to generate a pumping current;

adding a value proportional to the pumping voltage to a reference voltage to generate a variable reference voltage value;

controlling the pumping current to maintain a sensing voltage between the measurement electrode and the reference electrode substantially at the variable reference voltage value; and determining the value of the pumping current to determine an air to fuel ratio or oxygen concentration of a gas supplied to the sensor.

5. A method as claimed in claim 4, wherein the value proportional to the pumping voltage corresponds to ⅕ to ½ of the pumping voltage.

6. A method as claimed in claim 5, wherein the value proportional to the pumping voltage is determined on the basis of a structure of the wide range A/F ratio sensor.

7. A method of determining an oxygen concentration of a gas, comprising:

supplying the gas to gas sensor unit comprising:

a solid electrolyte plate;
a measurement electrode serving as both an oxygen pumping electrode and a sensing electrode;
a second pumping electrode; and
a reference electrode;

applying a pumping voltage between the measurement electrode and the second pumping electrode to generate a pumping current;

determining a variable reference voltage value comprising a sum of:
a constant reference voltage value; and
a variable value comprising a function of the pumping current or the pumping voltage;

controlling the pumping current to maintain a sensing voltage between the measurement electrode and the reference electrode substantially at the variable reference voltage value;

determining the value of the pumping current;

determining the oxygen concentration of the gas from the measured value of the pumping current.

8. A method of claim 7, wherein the gas comprises an exhaust gas, and determining the oxygen concentration of the gas comprises determining an air to fuel ratio of the exhaust gas.

9. A method of claim 7, wherein the variable value comprising a function of the pumping current or the pumping voltage comprises a surplus voltage; and wherein the surplus voltage comprises: $(I_p) \times (r_1) \times (r_3)/(r_2+r_3)$, where $I_p$ is the pumping current, $r_1$ is the resistance between the measurement electrode and the second pumping electrode, $r_2$ is the resistance between the second pumping electrode and the reference electrode and $r_3$ is the resistance between the reference electrode and the measurement electrode.

10. A method of claim 7, wherein the variable value comprising a function of the pumping current or the pumping voltage comprises a surplus voltage; and wherein the surplus voltage comprises: $(I_p) \times (kr_1)$, where $I_p$ is the pumping current, $kr_1$ is a variable resistance and $r_1$ is the resistance between the measurement electrode and the second pumping electrode.

11. A method of claim 7, wherein the variable value comprising a function of the pumping current or the pumping voltage comprises $KV_p$, where $V_p$ is the applied pumping voltage and $⅕ \leq K \leq ½$.

* * * * *

UNITED STATES PATENT AND TRADEMARK OFFICE
CERTIFICATE OF CORRECTION

PATENT NO. : 5,972,200
DATED : October 26, 1999
INVENTOR(S) : Byung-ki KIM

It is certified that error appears in the above-identified patent and that said Letters Patent is hereby corrected as shown below:

On the title page: [54] --WIDE RANGE AIR TO FUEL RATIO SENSOR AND METHOD FOR DRIVING THE SAME --.

Signed and Sealed this

Third Day of April, 2001

*Attest:*

NICHOLAS P. GODICI

*Attesting Officer*   *Acting Director of the United States Patent and Trademark Office*